(12) United States Patent
Maschke

(10) Patent No.: US 8,167,810 B2
(45) Date of Patent: May 1, 2012

(54) CATHETER DEVICE FOR TREATING A BLOCKAGE OF A VESSEL

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 842 days.

(21) Appl. No.: 11/636,679

(22) Filed: Dec. 8, 2006

(65) Prior Publication Data

US 2007/0135887 A1   Jun. 14, 2007

(30) Foreign Application Priority Data

Dec. 12, 2005 (DE) .................. 10 2005 059 261

(51) Int. Cl.
*A61B 8/00* (2006.01)

(52) U.S. Cl. ........ 600/466; 600/462; 600/467; 600/470; 600/478; 604/96.01; 606/194; 623/1.1; 623/1.2

(58) Field of Classification Search .................. 600/462, 600/466, 467, 470, 471, 478, 407; 604/96.01, 604/22; 606/159, 191, 194; 623/1.1, 1.11, 623/1.2

See application file for complete search history.

(56) References Cited

U.S. PATENT DOCUMENTS

| 5,093,877 A | 3/1992 | Aita et al. |
| 5,722,979 A | 3/1998 | Kusleika |
| 5,741,210 A | 4/1998 | Dobrovolny |
| 5,921,926 A | 7/1999 | Rolland et al. |
| 6,152,878 A | 11/2000 | Nachtomy et al. |
| 7,247,162 B1* | 7/2007 | Thornton ................. 606/200 |
| 7,289,842 B2* | 10/2007 | Maschke ................. 600/478 |
| 2002/0007215 A1* | 1/2002 | Falotico et al. ......... 623/1.21 |
| 2002/0049375 A1* | 4/2002 | Strommer et al. ....... 600/407 |
| 2003/0163190 A1* | 8/2003 | LaFont et al. .......... 623/1.11 |
| 2003/0236443 A1* | 12/2003 | Cespedes et al. ......... 600/29 |
| 2004/0059280 A1 | 3/2004 | Makower et al. |
| 2005/0101859 A1 | 5/2005 | Maschke |
| 2005/0171591 A1* | 8/2005 | McHale et al. ......... 623/1.11 |
| 2005/0222594 A1 | 10/2005 | Maschke |
| 2005/0222596 A1 | 10/2005 | Maschke |
| 2005/0222649 A1 | 10/2005 | Capuano et al. |
| 2005/0273130 A1* | 12/2005 | Sell ..................... 606/192 |
| 2006/0116571 A1* | 6/2006 | Maschke et al. ........ 600/424 |
| 2006/0246107 A1 | 11/2006 | Harder et al. |
| 2006/0287595 A1* | 12/2006 | Maschke ................. 600/424 |
| 2008/0177183 A1* | 7/2008 | Courtney et al. ........ 600/463 |
| 2009/0196899 A1* | 8/2009 | Birdsall et al. .......... 424/423 |

FOREIGN PATENT DOCUMENTS

| DE | 198 27 460 | * 12/1988 |
| DE | 9108314 U1 | 1/1992 |
| DE | 698 24 988 T2 | 10/1998 |
| DE | 198 27 460 A1 | 12/1998 |
| DE | 102 53 634 A1 | 5/2004 |

(Continued)

OTHER PUBLICATIONS

Internal Communication listing cited reference (typo error in translated US application), received Feb. 1, 2012, pp. 1.

(Continued)

*Primary Examiner* — Brian Casler
*Assistant Examiner* — Amanda Lauritzen

(57) ABSTRACT

The invention relates to a catheter device for treating a blockage of a vessel, with the catheter device featuring a treatment catheter for treating the vessel blockage which is embodied as an integrated unit with front-mounted stent.

12 Claims, 6 Drawing Sheets

FOREIGN PATENT DOCUMENTS

| | | |
|---|---|---|
| DE | 103 43 808 A1 | 5/2005 |
| DE | 10 2004 015639 A1 | 10/2005 |
| DE | 10 2004 015640 A1 | 10/2005 |
| EP | 0 832 616 A1 | 4/1998 |
| EP | 1 188 417 A2 | 3/2002 |
| EP | 0 885 594 B1 | 4/2003 |
| WO | WO 98/02084 A2 | 1/1998 |
| WO | WO 01/11409 A2 | 2/2001 |
| WO | WO 03/082363 A1 | 10/2003 |

OTHER PUBLICATIONS

US 5,924,990, 07/1999, Nachtomy et al. (withdrawn)*

* cited by examiner

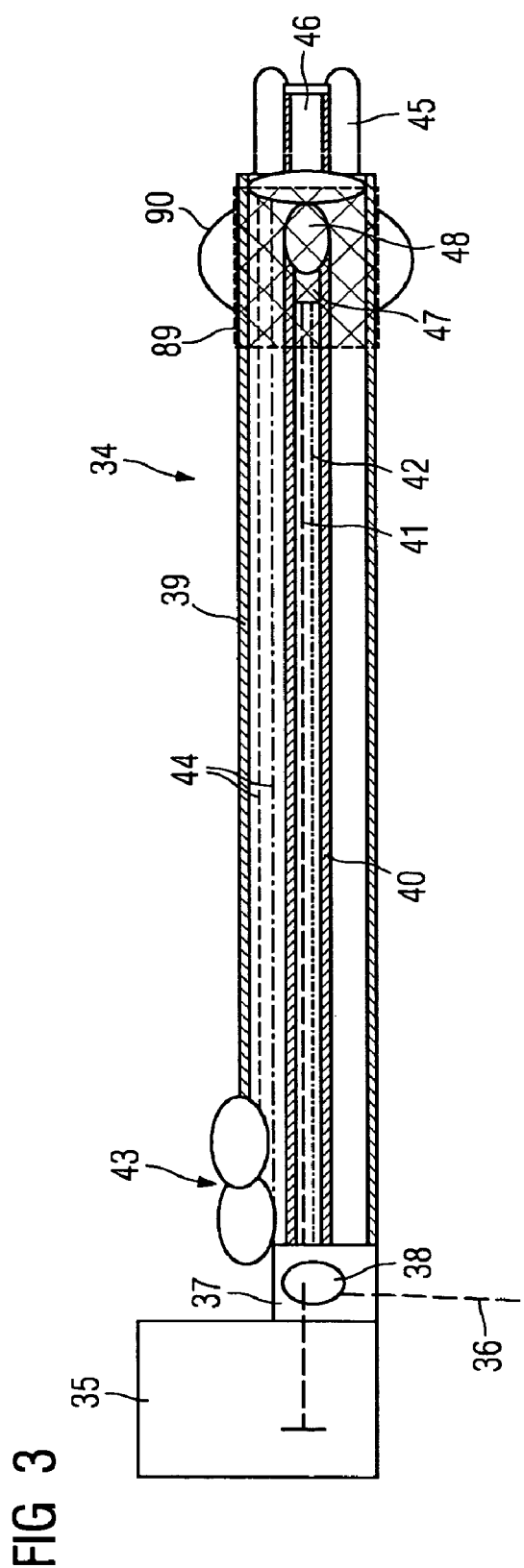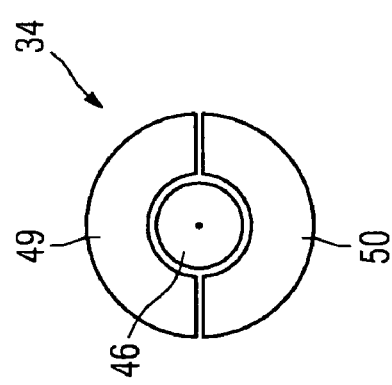
FIG 3
FIG 4

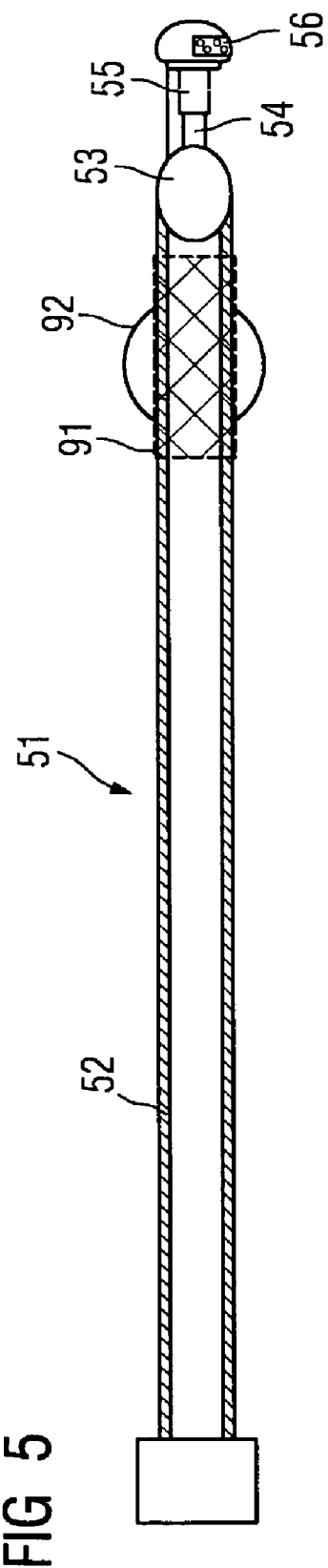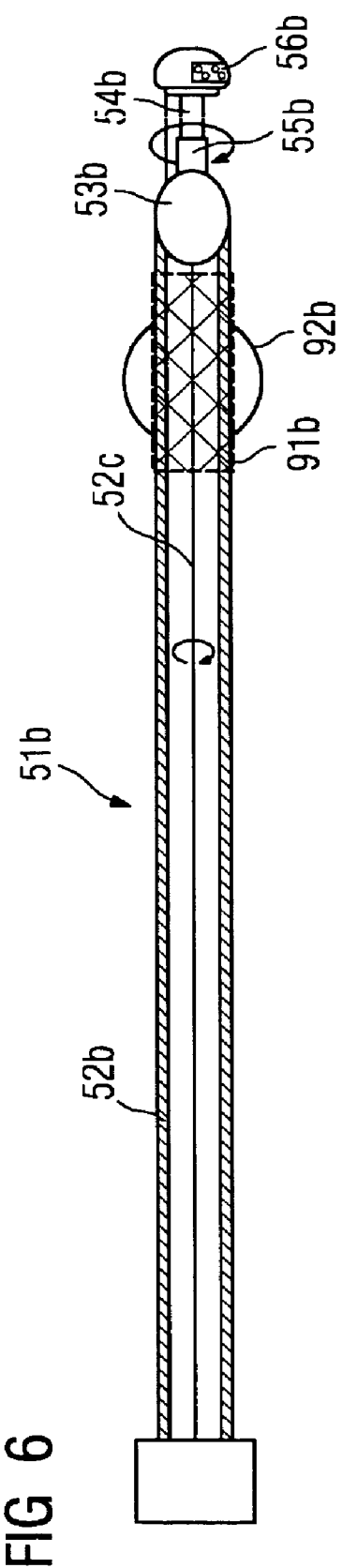
FIG 5
FIG 6

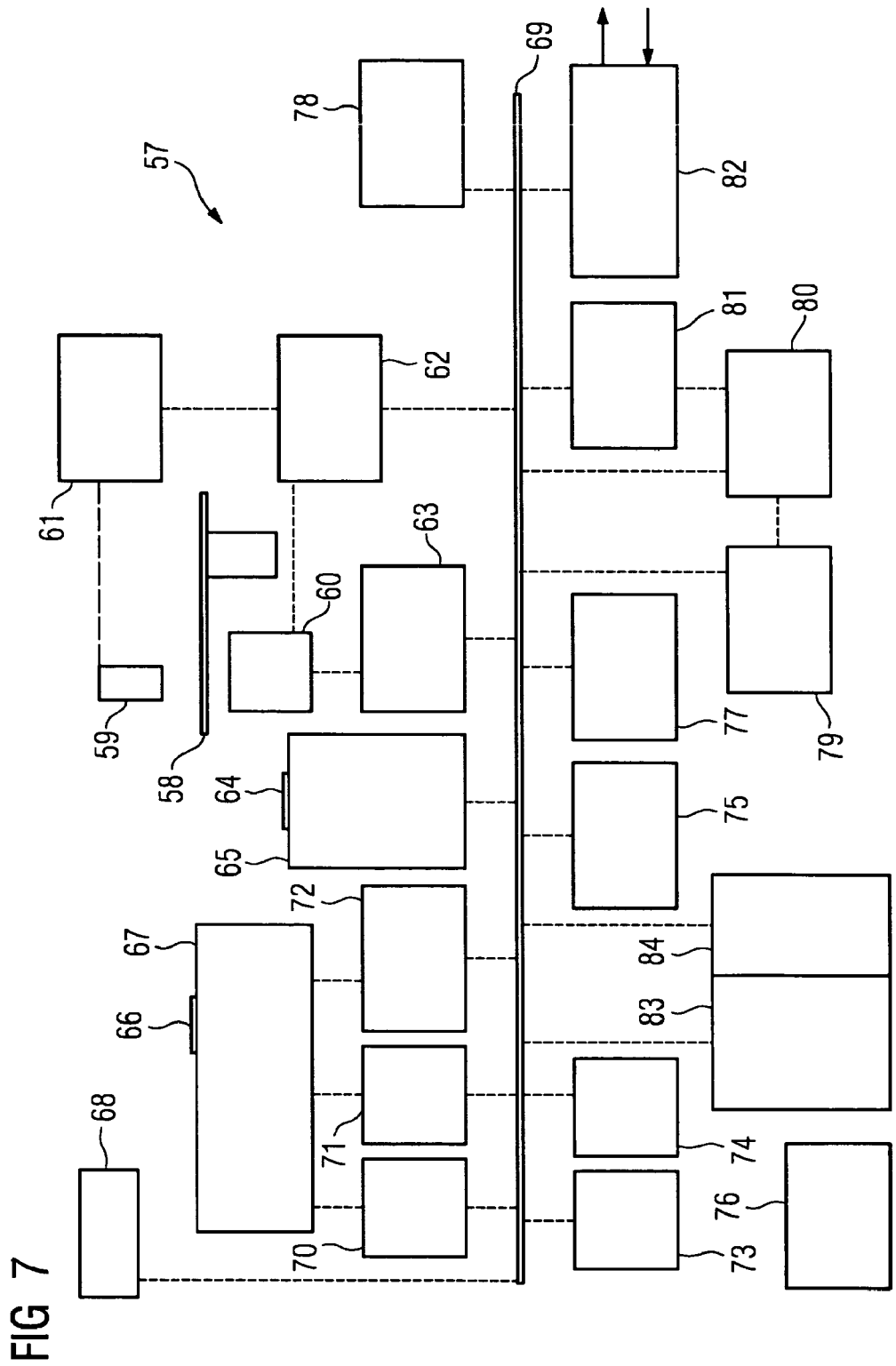

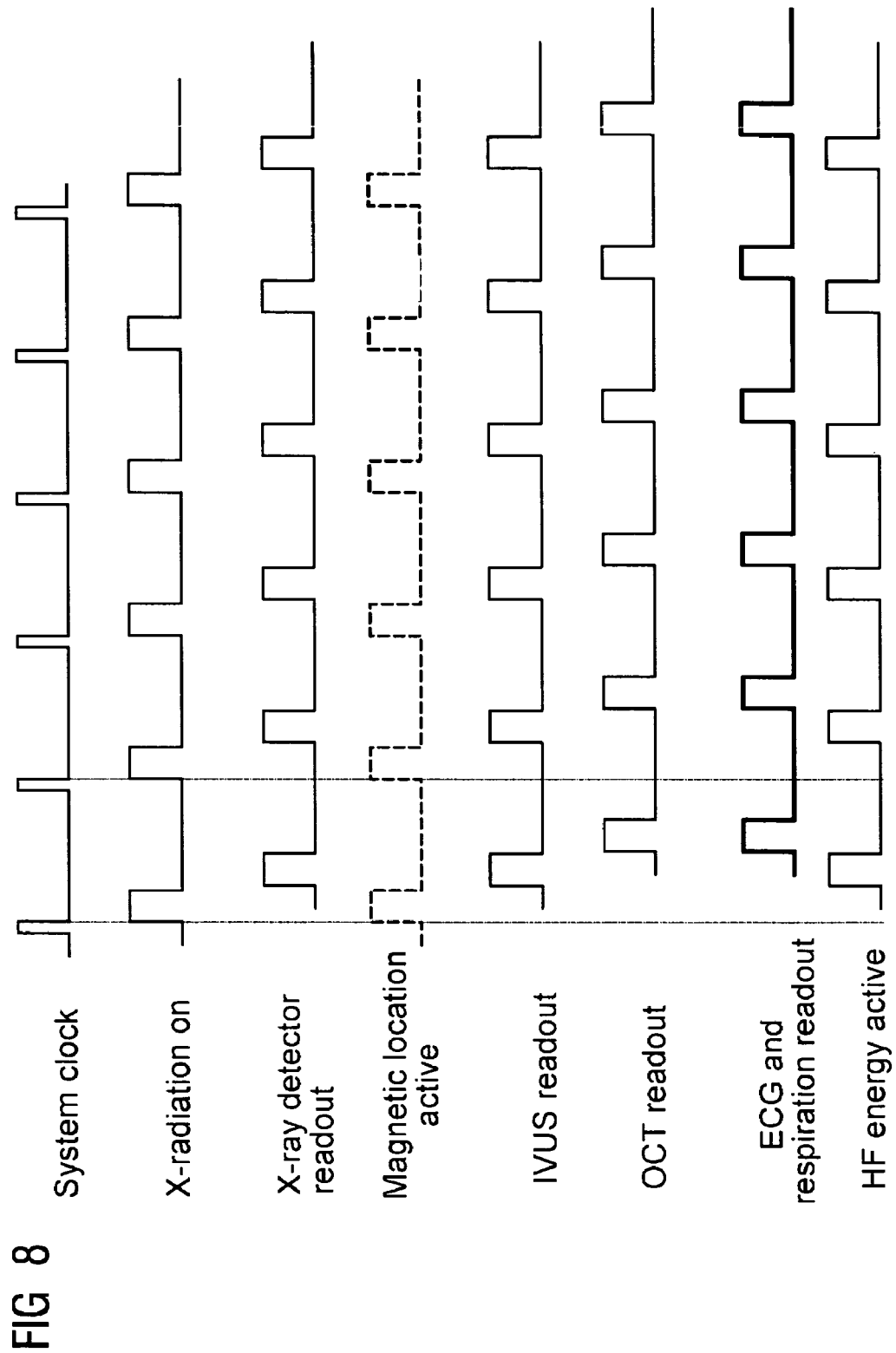

CATHETER DEVICE FOR TREATING A BLOCKAGE OF A VESSEL

CROSS REFERENCE TO RELATED APPLICATIONS

This application claims priority of German application No. 10 2005 059 261.9 filed Dec. 12, 2005, which is incorporated by reference herein in its entirety.

FIELD OF THE INVENTION

The invention relates to a catheter device for treating a partial and/or complete blockage of a vessel as well as to an associated x-ray device and a method for image monitoring during the treatment of the vessel blockage.

BACKGROUND OF THE INVENTION

Diseases of the vascular vessels currently represent one of the most frequent diseases with fatal outcomes. Particular mention should be made here of coronary infarction caused by diseases of the coronary vessels. Arteriosclerotic plaque results in a blockage of the coronary vessels, which can take a more or less serious form.

In recent years different methods for treating such narrowings of for example the coronary vessels or at other points in the vessel system have emerged. In such cases the attempt is made to remove the plaque or to destroy it and/or to expand the vessel in order to remedy the blockage of the vessel in this way. Interventions of this type for treating partly or completely blocked vessels are mostly carried under x-ray control with an angiography system. However in such cases the vessels involved, such as the coronary vessels for example, only appear as a two-dimensional silhouette. To make the vessel clearly visible additional contrast means must be injected into the vessel, and if for example the vessel is completely blocked, these means do not reach all areas of the vessel. In such cases the problem arises of some patients suffering from contrast means allergies or of the contrast means producing a hot feeling. In addition to this it is possible for the patient to suffer radiation damage.

On the other hand, because of the very restricted imaging, even with the provision of contrast means, it is very difficult for the medical personal to differentiate between plaque and vessel wall during the intervention. This increases the risk or removing or destroying tissue at the wrong places, so that injury to the vessel wall can result for example.

In as far as attempts have been made to rectify these types of problem by additional image monitoring as well as x-ray monitoring there has previously been the problem that, depending on the type of additional image monitoring, only a restricted local resolution or a good resolution only in the local area but not an entirely satisfactory representation can be achieved.

It is often necessary in treatment of diseases of vascular vessels, in order to support the opening of the vessel, to introduce a stent, i.e. a vessel support which mechanically stabilizes the vessel wall. A further expansion of the vessel can be achieved with stents for example. To introduce such stents it has previously been necessary to remove the catheter, on which there is provision for the treatment tool for the treatment of the vessel constriction again and subsequently to introduce the stent with a second catheter. This process is stressful for the patient however and involves risks, especially as regards the occurrence of a restenosis.

SUMMARY OF THE INVENTION

The underlying object of the invention is thus to specify a catheter device which is improved with regard to the above-mentioned problems.

To achieve this object a catheter device of the type mentioned at the start is provided featuring a treatment catheter for treating the vessel constriction which is embodied as an integrated unit with a front-mounted stent.

In addition the catheter device can be embodied with integrated image monitoring. In particular the treatment catheter can be embodied as an integrated unit with an OCT catheter and/or with an IVUS catheter. The treatment catheter can also be embodied with a position sensor system.

The abbreviation OCT stands for "Optical Coherence Tomography", of which the basic principle is based on the Michelson interferometer. OCT catheters enable image data to be recorded which allows a very good local resolution particularly in the local area.

If such a catheter is introduced separately into the vessel, the problem which arises is that, for further treatment of the vessel blockage with the treatment catheter, the separate OCT catheter must be withdrawn again from the vessel each time in order to subsequently introduce the treatment catheter.

This is avoided by an inventive catheter device in which the OCT catheter is embodied as a combination catheter with the treatment catheter in one integrated unit.

In addition the integrated unit may feature an IVUS catheter which is based on the technique of intravascular ultrasound and with which additional image data can also be obtained. This makes it possible not only to map the state of the lumens of vessels but also to create an image of the vessel walls. The ultrasound method alone however only offers a restricted local resolution. If an IVUS catheter is embodied as a separate catheter, like the OCT catheter, this has to be additionally introduced and once again removed from the vessel before the introduction of the treatment catheter, which makes treatment more difficult and imposes greater strain on patients. This is avoided by an inventive integrated solution.

A conventional IVUS system is described for example in DE 0 885 594 B1, whereas the use of OCT technology is known from WO 01/11409 A2 or U.S. Pat. No. 5,921,926.

In the inventive catheter device these two options of imaging by means of an OCT catheter and an IVUS catheter may be integrated into the treatment catheter so that a combination catheter is embodied for treatment and image monitoring. In addition a position sensor system is expediently provided which enables precise localization of the catheter device in the body of the patient. Thus an integrated combination with which an optimum diagnostic imaging and minimally invasive medical treatment becomes possible replaces the previous part or individual solutions. The treatment catheter enables the device to dissolve the vessel blockage, and simultaneously through different imaging methods OCT and IVUS, enables it to provide a good visibility of the catheter in relation to the vessel, to which end the position sensor system for locating the device is additionally used, in order to create images with high spatial resolution in the local area and remote area of the vessel blockage.

The image information of the OCT and IVUS images can be combined in this case, for example for creating overlay images, with a combination with data from conventional x-ray monitoring or similar also being possible. Thus two-dimensional or especially also three-dimensional images with high diagnostic quality can be obtained, whereby the embodiment of the device as combination catheter does away with a temporary withdrawal of one or both imaging catheters and a re-introduction of the treatment catheter with the corresponding disadvantages for the patient as well as for the doctor performing the treatment. This means that the combination of the two imaging methods OCT and IVUS with a treatment catheter allows optimum treatment of vessel blockages using image monitoring, in which more detailed image information will be obtained in all imaging areas, i.e. both in the local and also in the remote area.

The OCT and the IVUS catheter in this case each feature signal lines which lead to the catheter tip, at which the sensors for the optical coherence tomography or the intravascular ultrasound are provided. The OCT sensor can in this case be embodied as a rotating mirror, on which the light signals sent out for detection of interferences are reflected.

The catheter device features a front-mounted stent used to support the vessel. The fact that such a stent, which is of course also taken to mean a number of separate devices or stents used for supporting the vessel is arranged on the one integrated catheter for treatment of the vessel blockage obviates the need for removal of another catheter, which has been used for example to remove the plaque. The combination catheter allows the stent to be introduced at the same time as the treatment tools. This results in a reduced risk of restenosis.

Overall this allows a single catheter to be used for treatment, with which both the vessel blockage can be removed, if necessary using the appropriate image monitoring, and a stent maintaining the opening can be introduced into the vessel. The treatment thus requires fewer treatment steps, with the appropriate embodiment also providing the option of monitoring the process using three-dimensional images. The presentation of the local area can be guaranteed with a combination of OCT and IVUS while sufficiently good images of layers of the vessel deeper down are simultaneously obtained. By utilizing the signals of a position sensor the disposition and movement of the integrated treatment catheter can be mapped with the aid of the IVUS, OCT and the specified, for example electromagnetic signals of the position sensor system, so that the x-ray radiation to which the patient is subjected can be reduced.

The stent can be front-mounted in the area of the catheter tip. The device for supporting the vessel is thus positioned right from the start in the treatment area, so that subsequently without any greater movement of the catheter the stent can be placed at the correct location at which the treatment has been undertaken.

An expandable balloon can also be placed in the area of the tip of the catheter, with the front-mounted stent being able to be placed and/or attached depending on the expansion of the balloon. The stent is thus pressed into the vessel wall as the balloon fills up and thereby attached. The stent can be arranged on the balloon in the non-unfolded state or is located in the area of the balloon, so that, when the balloon is inflated, the disposition of the stent in relation to the vessel is influenced. For example the stent can be deformed or overstretched beyond its elastic limits when the balloon is unfolded so that the shape arising as a result of the inflation of the balloon is retained afterwards. In this way the stent is explicitly formed and disposed with the aid of the balloon or attached or anchored in the vessel area.

The stent can also be embodied to at least partly unfold itself automatically. In this case for example an envelope made of a plastic material at least partly surrounding the stent is removed, after which the corresponding area of the stent unfolds. As a rule either a stent which unfolds with the aid of a balloon is used or a self-unfolding stent. It is however also conceivable to combine these two options for introducing or attaching the stent in the vessel area.

In addition the stent can be embodied at least from metal, especially stainless steel or nitinol. As a rule mesh or net arrangements are used for stents, consisting for example of steel or a specific metal or other metal alloys, for example nickel-titanium alloy, nitinol or other memory-metal alloys.

In addition the stent can be embodied at least partly from bioabsorbable material, especially from biological material and/or magnesium and/or bio engineering material and/or plastic. Polymers can be used for example. With bioabsorbable materials the advantage lies in the fact that these dissolve after a certain time which under some circumstances can be predefined, so that the stent, if it is no longer necessary to support the vessel after a certain time, can automatically break down and thereby be removed without any further intervention and without presenting any risk for the patient. Naturally other advantageous materials and material combinations can be used for the stent which have positive effects on the inner surface of the vessel or are able to support the vessel and maintain the opening in it. In addition requirements regarding the options for introduction and visualization for checking examinations are to be adhered to for example. In addition the characteristics of the stent materials with regard to their influence on the blood flow or the occurrence of blood clots are to be noted.

The stent is advantageously embodied with a coating, especially with a nano coating and/or a drug agent coating. These types of coatings for example allow the guidance of the catheter device, on which the stent or stents are front mounted, to be improved. A coating with drug agents or medicaments which are released over the course of a specific period of time is used for example to check the cell division of the cells in the vessel wall. In addition the release of the appropriate drug agents or medicaments, which are released as soon as the stent is placed in the area of the vessel, can further reduce the risk of restenosis.

Examples of possible agents are Sirolimus, Paclitaxel, Everolimus and/or Rapamycin as well as FK 506.

Furthermore the catheter can be embodied with a device to advance it or withdraw it automatically. This allows the integrated catheter to be introduced into the vessel or removed from it again at a defined speed, which can enable complications arising for example from manual guidance which is too hasty or too imprecise to be avoided.

In accordance with the invention the catheter for treating the vessel blockage can be a CTO catheter for treating a complete vessel blockage, especially a pincer-type catheter and/or a radiation-based catheter, or a catheter for treating a partial vessel blockage, especially a laser angioplasty catheter.

The abbreviation CTO here stands for "Chronic Total (Coronary) Occlusion", that is for a complete blockage, especially of the coronary vessels. Expanding pincers can be used for handling these types of blockages which push the plaque in the vessels apart piece-by-piece and thus allow a step-by-step removal of the vessel blockage. It is also possible to use high-frequency energy with which the plaque can likewise be removed.

A further method for treatment of a vessel blockage is what is known as laser angioplasty, in which the plaque is destroyed or removed with a thermal or non-thermal laser using heating of a laser balloon catheter or using an ultraviolet pulsed laser. To enable laser angioplasty to be used a residual lumen is required in the vessel however.

The selection of the sensible type of treatment thus depends on the type of blockage and the blockage geometry, taking into consideration the risks and costs. In each case an expediently-selected treatment catheter as a combination catheter in an integrated unit with a stent and also possibly position sensors and OCT and IVUS sensors for improved imaging is provided with the inventive catheter device.

The signal lines of the OCT and/or of the IVUS catheter can be routed within the catheter shell of the catheter for treatment of the vessel blockage, especially within a hollow drive shaft of the OCT and/or IVUS catheter. The treatment catheter itself can be embodied in this case as a tubular catheter with a catheter shell with at least one or more lumina. Within this catheter shell of the treatment catheter, which has a rather greater diameter as regards its function, the signal lines for the OCT and the IVUS imaging which connect the OCT and IVUS sensors at the tip of the catheter device to a signal and/or drive unit are guided, if necessary in lumina. Expediently a common drive shaft or separate drive shafts are present for the OCT and the IVUS catheter in order to allow independent movement of the two catheters if necessary. The relevant signal lines are expediently routed in a protected manner where necessary in such a drive shaft embodied with a hollow inner space.

The OCT and/or IVUS catheter and/or a surrounding drive shaft can be embodied to allow them to rotate. If instead of an outer drive shaft only the IVUS or OCT sensor rotates, which is connected to its signal lines in each case, there is no friction between the catheter device and the vessel wall. A rotation of the IVUS or OCT catheter rotates an image sensor embodied for example as a mirror for OCT. Instead of an external drive shaft there can of course be a drive shaft present within an outer catheter shell which can also rotate.

The image sensor of the OCT and/or IVUS catheter can be arranged in front of or behind a treatment unit, especially a pair of pincers or a coil or a laser lens, of the catheter for treatment of a vessel blockage. Depending on the type of arrangement for example in front of or behind a coil for creating high-frequency energy for plaque removal, images can be created which show the removal of the plaque for example or the front area of the vessel in which the radiation energy of a laser is already operating or the pincers to remove plaque in a further operation. Thus different information can be obtained as regards a further treatment sequence or the assessment of a treatment just performed or still in progress.

The treatment unit can furthermore feature an opening for feeding through a movable drive shaft and/or the signal lines of the OCT and/or of the IVUS catheter. When such an opening exists it is possible to place the image sensors in front of or behind pincers or a laser lens or such like, as required, by feeding them through the opening for the hollow drive shaft and/or the signal lines or sensors. Thus the imaging with the combined catheter device is not adversely affected by the treatment unit, but comprehensive imaging of the entire treatment area is also possible without removing the treatment unit.

The catheter device can feature at least one transparent exit area for the ultrasound of the IVUS catheter and/or the light of the OCT catheter. Thus for example a surrounding catheter shell of the device can feature one or more transparent exit windows in the area of its tip which are transparent for infrared light or ultrasound and thus allow imaging. It is of course also conceivable for an entirely transparent design or a transparent design not only in the area of the tip of the catheter device to be provided.

For three-dimensional imaging the catheter device can be embodied for rotation and for simultaneous withdrawal and/or advance of the OCT catheter and/or of the IVUS catheter. By rotating the two image sensors or one of the image sensors while simultaneously withdrawing or advancing them it is possible to create three-dimensional images with the combination catheter. In this case it is conceivable on one hand for the two image sensors to rotate and simultaneously for both to be moved in a longitudinal direction, for example both forwards. With an appropriate embodiment of the drive it is however also conceivable for both image sensors to be rotated and for example the OCT catheter to be moved forwards while the IVUS catheter moves backwards or alternately moves slightly forwards and backwards.

In accordance with the invention the position sensor system can be embodied electromagnetically or on the basis of ultrasound. Through position sensors at the tip of the catheter it is possible to obtain an exact three-dimensional representation of the vessel since movement artifacts can be prevented through the size relationships of the catheter relative to the vessel. To do this suitable mathematical methods are used to approximate the center line of the vessel and where necessary of the vessel envelope curve and the corresponding information is combined with the sensor positions. This makes exact, offset-corrected three-dimensional reconstruction possible.

With the aid of electromagnetic position sensors three-dimensional images can be created from the initial two-dimensional OCT or IVUS images which allow a significantly better assessment of the treatment. Parts of the electromagnetic transmitter or also of the receiver can be arranged in the catheter, which in turn leads to the corresponding arrangement of the transmitter or receiver outside the body. For location within space at least one transmitter is assigned to one receiver or vice versa, whereby under some circumstances a combination of two transmitter devices with one receiver or vice versa can be possible, with known angular relationships for example. If the coils of an electromagnetic positioning system are not arranged exclusively orthogonally to each other, but at random angles of for example 60°, the corresponding coil unit can be reduced in size, so that it can be arranged in the catheter without any problems.

The position sensors are expediently arranged in the area of the catheter device tip. This makes location within the area possible, which is also of particular interest for imaging using the OCT or IVUS method. After the installation of an examination device with an inventive catheter device with a position sensor system a calibration is advantageously undertaken and magnetic field sequences are stored as templates.

The catheter device can be embodied for automatic mechanical navigation and/or for magnetic navigation. For an automatic mechanical navigation calculated movements can be reliably and stably implemented using robot technology. In addition magnetic navigation of the combination catheter is also possible, in which the catheter provided with magnets is controlled and driven by an external magnetic field. This can be done using permanent magnets or electromagnets.

Advantageously at least one movement sensor for detection of possible patient movements is provided in accordance with the invention. This enables artifacts caused by such movements to be detected in advance of image computation and excluded from the computations or taken into consideration. A mathematical movement detector can be provided for this purpose or sensors with different operating principles, for example electrical or acoustic sensors or such like, can be used. The data can be transmitted over a cable connection or also a wireless connection to an appropriate processing unit. The use of RFID technology is also possible. Movements of organs, caused by a heartbeat for example, can be taken into account using further sensors, by measuring the breathing amplitude or recording an ECG or such like.

In addition at least one physiological sensor can be provided at the tip of the device. This enables micro or nano sensors to be used to measure temperature or pressure or to determine a ph value and such like. In this way additional information is obtained which enables a decision to be made about continuing the treatment or indicates whether the treatment is proceeding without complications.

The catheter device can have a coating for screening and/or improved guidance of the catheter device in the vessel. A screening can prevent magnetic interference fields which may interfere with the recorded signals. One option for such screening is provided by a thin-film layer of nano particles. In addition thermal isolation can be required to protect the electronic components and sensors against a coolant. It is possible using a corresponding coating of the combination catheter to reduce the friction resistance when the catheter is guided or fed through the vessels. Suitable coatings here are a silicon coating or a coating using nano technology materials.

An image sensor of the OCT catheter can be arranged in a longitudinal direction of the catheter device in front of or behind an image sensor of the IVUS catheter. The OCT sensor which is arranged in front of the IVUS sensor can thus be arranged at the tip of the catheter device in the direction of the treatment to be performed. Alternatively however the order of the sensors can also be reversed. The only decisive factor is how an optimum image monitoring can be achieved in the case concerned.

The catheter device can additionally feature a lumen, especially a separate lumen which is embodied for injection of an ultrasound contrast means. It is thus possible, using a lumen which is present in any event or an additional lumen, to inject an ultrasound contrast means in order to further improve the imaging of the IVUS catheter in this way.

In addition the invention relates to an x-ray device which is embodied with a catheter device as claimed in one of the previous claims. Such an x-ray device thus features a radiation source which is connected to a corresponding system control and generates x-rays with which a patient can be radiologically treated on a corresponding support device. The x-ray images created with the image data and other data which were recorded by the catheter device inserted into the body of the patient with the OCT and IVUS sensor can be combined for evaluation or placed in context via a data bus. The results of the image processing can be presented to the doctor before in the treatment at a display unit of the x-ray device. The treatment of the vessel blockage, such as the removal of plaque or the unfolding of the stent can be traced with the optimum visual monitoring, where necessary throughout the entire treatment.

To this end the x-ray device can be embodied to combine and/or overlay the OCT and/or IVUS data with x-ray data and/or image data of other modalities. The combination catheter images created can be displayed together with the x-ray images using a shared user interface and are thus easily visible at a single defined location for the user so that a rapid and improved diagnosis creation and handling is possible. The very widest range of overlay options of two-dimensional and three-dimensional or two-dimensional and three-dimensional images through to four-dimensional recordings of the angiographic x-ray images and the images of the combination catheter for segmentation, registration and image diffusion produces hitherto unknown diagnostic and handling advantages. The images can be overlaid with images of the modalities such as a sonography, magnetic resonance tomography and such like which have been produced in advance of the treatment or are being created in parallel in a hybrid system, that is in combination with the x-ray device.

In accordance with the x-ray device can feature at least one image correction device which is embodied for correction of image artifacts caused by the stent. Expediently an image correction unit which is present in any event, i.e. a correction processor for image processing units for the IVUS, the OCT as well as the x-ray imaging or for the processing of the sensor signals is used here. The image correction in this case is based on knowing the structure of the stent or the stents introduced, so this stent or these stents can be taken into account in the image reconstruction. This enables image artifacts or problems which the image display to be explicitly edited out.

Furthermore the invention relates to a method for image monitoring in the treatment of a partial and/or complete vessel blockage by means of a catheter device which features a catheter for treatment of the vessel blockage which is embodied as an integrated unit with a front-mounted stent as well as an OCT catheter and/or an IVUS catheter and/or a position sensor system for image monitoring. With this method image monitoring is performed within the context of treating a vessel blockage in which a catheter device as described above is used. To this end the catheter is initially introduced under x-ray control and where necessary supplementary supply of contrast means and for example angiographic overview images are created it necessary. After this the images of the electromagnetic position sensors or if necessary of another positioning system are created. These images can be overlaid with the images of the overview angiography and the catheter is navigated on the basis of the images through to its target position in the vessel. These steps can in part be undertaken in parallel and automatically without the intervention of the user.

If a desired target position is reached a flushing fluid for optical coherence tomography can be injected it necessary and the blockage of the vessel can be observed by OCT and IVUS images in two or in three dimensions at high resolution. With the aid of the electromagnetic position sensor a three-dimensional reconstruction can be undertaken and a subsequent overlaying with the overview angiography. The treatment unit, that is for example the pincers of the CTO catheter or the laser lens of the laser angioplasty catheter, is placed at the position in the vessel envisaged for the treatment and the placement is checked using the OCT and IVUS data. Subsequently the vessel blockage is opened or rectified, with the process being repeated until plaque has been removed on all sides over the appropriate length.

After a renewed check by the image monitoring the opened blockage can be finally assessed. CTO catheters can in this case, in addition to the use of pincers and high-frequency energy, be based on a therapeutic ultrasound, and produce vibrations, be based on refrigeration technology but also a have retractable wires or needles as well as rotation devices and devices for emitting chemical or biological substances. The opening of the vessel is held open with the stent, which, in order to do this, unfolds from its front-mounted position and is placed in the vessel, by a balloon provided for this purpose being expanded for example. After successful treatment and positioning of the stent the catheter can be removed.

In addition an application of the method is possible not only in coronary vessels but in general in the vessel-type hollow spaces in human or animal bodies, that its in hollow spaces of organs for example.

The treatment can thus be carried out without the need for certain method steps such as the removal and reintroduction of imaging catheters or separate catheters carrying stents. In addition only the combination catheter is required for treatment, that is the end effect is to have a single catheter compared to the previously used separate catheters. Good images can be generated in the local area using OCT imaging whereas IVUS imaging makes possible a good imaging in the surrounding vessel layers. Three-dimensional images can be reconstructed with the aid of the position sensor system and the doses of X-ray radiation applied can be reduced if necessary. As well as additional information about the blockage and the plaque the correct position, especially of the treatment unit, can be better checked.

BRIEF DESCRIPTION OF THE DRAWINGS

Further advantages and details of the invention emerge with reference to the following exemplary embodiments as well as the drawings. The Figures show:

FIG. 3 an inventive catheter device with a pincer-type CTO catheter which features an opening for the OCT and IVUS sensor, FIG. 4 a cross-section of the tip of the catheter device of FIG. 3, FIG. 5 an inventive catheter device with a high frequency-based CTO catheter and a drive shaft, FIG. 6 an inventive catheter device with a high-frequency-based CTO catheter and a sealable OCT and IVUS catheter, FIG. 7 an inventive x-ray device with a CTO catheter device and FIG. 8 a schematic diagram for sensor readout when executing an inventive method with the x-ray device shown in FIG. 7.

DETAILED DESCRIPTION OF THE INVENTION

Figure 1:
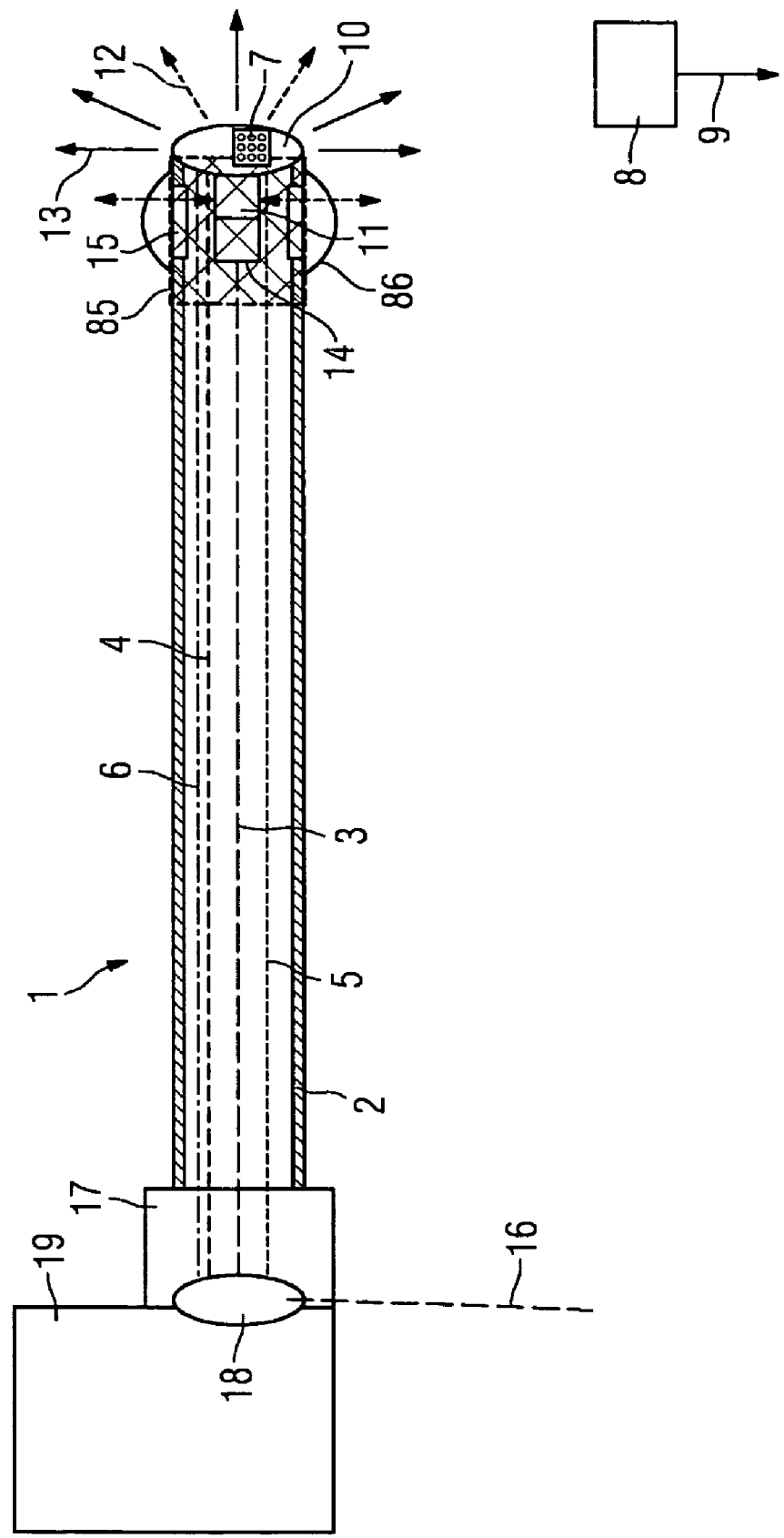
FIG. 1 an inventive catheter device with a laser angioplasty catheter.

FIG. 1 shows an inventive catheter device 1 with a laser angioplasty catheter. The inventive catheter device 1 features a hollow flexible drive shaft 2 in which an OCT signal line 3 and an IVUS signal line 4 are integrated. The OCT signal line 3 is embodied as a glass fiber line in this case. In addition a signal line 5 of the position sensor system which is embodied as an electromagnetic sensor system, and a signal line 6 for the laser energy for performing the laser angioplasty are arranged in the flexible drive shaft 2, with said lines being optical fibers. Thus the surrounding drive shaft 2 produces an integrated unit and which embodies a combination catheter which replaces previously used separate catheters, with the benefit of better image monitoring and treatment of vessel blockages.

A preferred embodiment is an embodiment not shown here in which the drive shaft 2 does not rotate but only the IVUS and the OCT sensor in order where necessary to avoid friction between the catheter device and the inner wall of the vessel and at the same time effect a rotation of an OCT sensor.

The signal line 5 of the electromagnetic position sensor system leads to antennas 7 arranged at the tip of the catheter device 1, which are arranged in the x-, y- and z-direction and which are merely shown schematically here. The antennas 7 interact with an emitter and/or receiver system 8 outside the body, which in its turn features position sensors or detectors. From here the data, as indicated by the arrow 9, is forwarded via a corresponding interface to a position detection unit.

A lens 10 for emitting laser light or laser energy, which is used for the treatment of the vessel blockage, is activated via the line 6. The lens 10 is embodied to be partly transparent for ultrasound in this case so that the ultrasound signals of an IVUS sensor 11 which are indicated here by dashed arrows 12 can penetrate the lens 10. The lens 10 emits the energy forwards or sideways, as shown here by the arrows 13.

An OCT sensor 14 connected to the OCT signal line 3 is embodied as a rotating mirror, whereby the OCT sensor 14 as well as the IVUS sensor 11 is arranged in the direction of advance of the catheter device 1 behind the lens 10. A transparent exit window 15 of the surrounding drive shaft 2 is provided in the area of the OCT sensor 14 or of the IVUS sensor 11 through which the infra-red light and ultrasound to make the imaging possible can emerge. The OCT sensor can, in an alternative not shown here, also be embodied as a rotating shaft on which a light exit or light entry windows present.

In the rear area of the catheter device 1 there is additionally a connection 16 for introducing a contrast means and/or flushing fluid. Operation of the catheter device 1 is made possible via a mechanical connection system 17 and a rotation coupling 18 for the connections. The catheter device 1 can in this case be advanced and withdrawn while a rotational movement for example of the OCT sensor is occurring. The catheter is advanced or withdrawn using an automatic advance and withdrawal device. Finally the signal and/or drive unit 19 is connected downstream which is used to create the movement as well as to generate signals and detect signals.

In addition the catheter device 1 features front-mounted stent 85 which is embodied as a metal wire net and is shown here in its non-expanded position. In alternative embodiments the stent can also consist of other materials such as bioabsorbable materials. When the treatment is completed with the aid of the lens 10, the stent 85 is expanded by means of the expandable balloon 86, for which the supply lines are not shown in this diagram for reasons of clarity. The balloon 86 is filled so that the stent arranged on it overextends in the direction of the vessel wall and is pressed into the vessel wall. The positioning of the stent 85 is monitored with the aid of the imaging sensors.

Thus a laser angioplasty treatment of a vessel blockage can be undertaken with the inventive combination catheter using optimum image monitoring by OCT and IVUS in combination with electromagnetic position sensors and a stent can be placed in the vessel.

Figure 2:
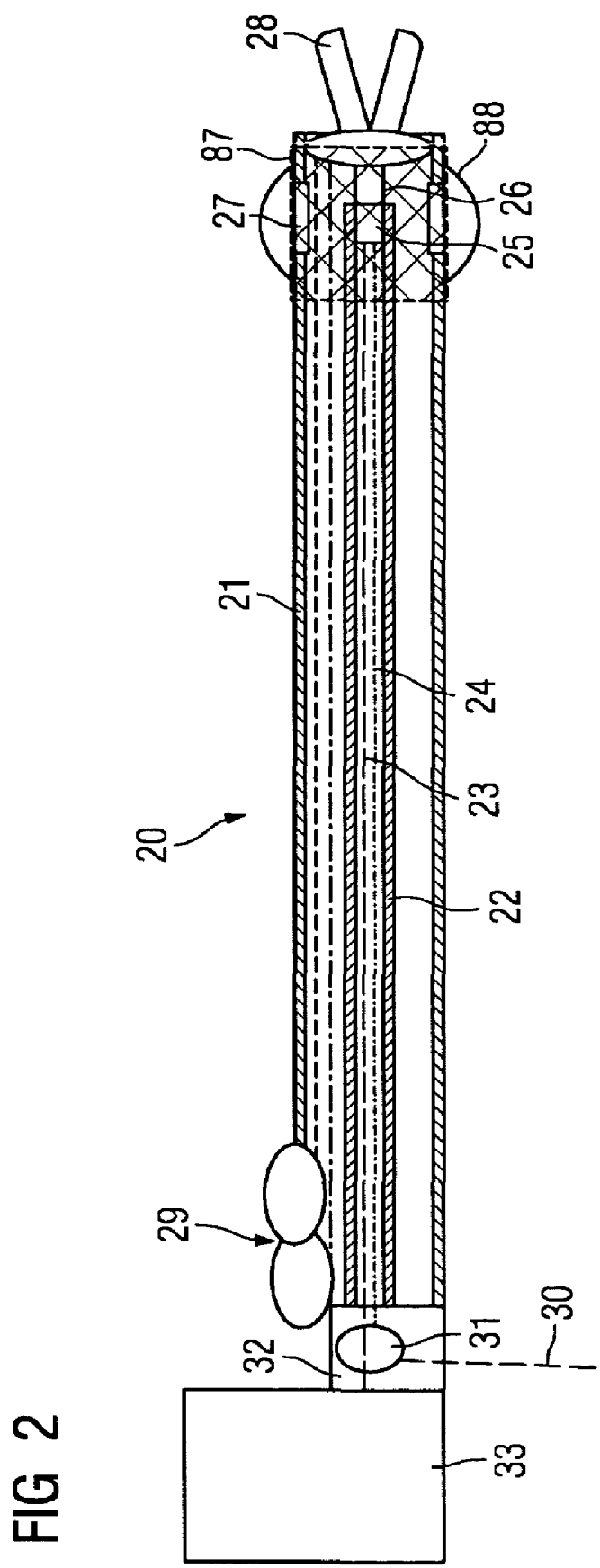
FIG. 2 an inventive catheter device with a pincer-type CTO catheter.

FIG. 2 shows an inventive catheter device 20 with a pincer-type CTO catheter. Here, in addition to a tubular catheter shell 21, a hollow flexible drive shaft 22 is again provided in the inner area of the catheter shell 21 in which an OCT signal line 23 as well as an IVUS signal line 24 are integrated. Signal lines 23 or 24 lead to an OCT sensor 25 which is embodied as a mirror, and to an IVUS sensor 26 arranged before it in the direction of the treatment to be performed. The catheter shell 21 features a transparent window ring 27 in its front area through which the light or ultrasound of the OCT sensor 25 and of the IVUS sensor 26 can escape.

For treatment of the complete vessel blockage "pincers" 28 are arranged at the tip of the catheter device 20 with which the plaque in the vessels can be pushed away piece-by-piece, in order to remove the complete vessel blockage in stages. In the rear area of the catheter device 20 is a mechanical device 29 for actuating the "pincers" 28 of the pincer-type catheter. In addition there is again a connection 30 for bringing in contrast media and/or flushing fluid, and also a rotation coupling 31 and a mechanical connection system 32. The imaging catheter is activated via a signal and/or drive unit 33. The recorded image signals are additionally fed back to the signal and/or drive unit 33 via the signal lines 23, 24 for further processing in order to create image recordings from them. The position sensor system also present is not shown here for reasons of clarity. This comprises an antenna system which interacts with a transmitter and/or receiver system, as shown in FIG. 1.

After the vessel blockage has been removed the front-mounted stent 87 is unfolded depending on the filling of the balloon 88 and is disposed in the vessel in order to support the latter. The stent 87 is provided with a medicament coating via which a defined quantity of medicament is released to prevent restenosis. Other exemplary embodiments are of course conceivable in which the stent does not have a medicament coating. This embodiment provides for a coating with the drug Sirolimus. As an alternative or in addition coatings with Paclitaxel, Everolimus or Rapamycin are possible. The structure of the stent 87 is known, so that the imaging is not adversely affected by this during the treatment.

FIG. 3 shows an inventive catheter device 34 with a pincer-type CTO catheter which features an opening for feeding through the OCT and IVUS sensor in its tip area. The catheter device 34 is activated via a signal and/or drive unit 35 which enables imaging operation. As well as a connection 36 for bringing in contrast media and/or flushing fluid, a mechanical connection system 37 for connection with the front part of the catheter device 34 and a rotation coupling 38 for the connections of the catheter device 34 are provided.

A hollow flexible drive shaft 40 is arranged in a catheter shell 39 in which the IVUS signal line 41 and the OCT signal line 42 are routed. A "pincer" 45 for dissolving the constriction of the vessel can be operated via a mechanical device with corresponding lines 44. The "pincer" 45 features an opening 46 through which an OCT sensor 47 and an IVUS sensor 48 can be moved, in order to record image data in advance of the "pincers" 45. In the arrangement of the OCT sensor 47 or of the IVUS sensor 48 images can also be recorded here via a corresponding transparent embodiment of the catheter shell 39. Thus the area for treatment can be recorded over a wide area and thereby the treatment or the progress of the treatment better assessed.

The catheter device 34 also features a front-mounted stent 89 which is unfolded with an expandable balloon 90 as a function of its unfolding process. The front-mounted stent 89, of which the expansion is not shown in this diagram is provided with a nano coating, so as not to adversely affect the guidance of the catheter device 34. Such a nano coating is preferably present, but is not required for each exemplary embodiment. The same applies to a medicament coating. This means that it is possible in accordance with the invention to fully treat the vessel blockage solely with the catheter device 34, including the introduction of the stent, without it being necessary to withdraw one catheter and introduce another one.

The position sensor system not shown in this diagram is embodied in the same way as in FIG. 1 and consists of internal antennas and an external transmitter or receiver system.

FIG. 4 shows a front view of the tip of the catheter device 34, in which an upper half 49 and a lower half 50 of the "pincers" 45 can be seen. The opening 46 is shown in the central area, through which the sensors 47 and 48 can move to record image data.

FIG. 5 finally shows an inventive device 51 with a high-frequency-based CTO catheter. The catheter device 51 again features a drive shaft 52 in which the glass fiber line for the OCT sensor as well the lines for the IVUS sensor the electromagnetic position sensor system and the optical fiber for activation of a coil 53 not shown in the drawing are accommodated. An emission of high-frequency energy is possible via the coil 53 in order to remove plaque in the vessel by this method. In the front area of the coil 53 an OCT sensor 54 is arranged, with an IVUS sensor 55 in front of it. In addition an antenna system 56 of the electromagnetic position sensor system is indicated. A vessel blockage can be rectified with the inventive catheter device 51 by emitting high-frequency radiation by means of the coil 53.

A front-mounted stent 91 of the catheter device 51 consists of a biological material which is dissolved after a predefined time, in which case complications arising from a stent 91 which is no longer required are avoided. Alternate materials are conceivable. The stent 91 is embodied to be partly self-unfolding. A balloon 92 is also provided to support the stent expansion which can be expanded via supply lines not shown in the diagram. In its expanded state the stent 91 presses against the vessel wall and is anchored in this.

FIG. 6 shows an inventive catheter device 51*b* with a high-frequency-based CTO catheter and a rotatable OCT and IVUS catheter. The catheter device 51*b* features a flexible catheter shell 52*b* which is embodied in a fixed position. A coil 53*b* allows the emission of high-frequency radiation for plaque removal. In front of the coil 53*b* an IVUS sensor 55*b* is initially arranged, in front of which an OCT sensor 54*b* is connected. The OCT sensor 54*b* and the IVUS sensor 55*b* are controlled via the signal lines 52*c* which are shown in simplified form in this figure. Furthermore an antenna system 56*b* is again provided for a position sensor system. A front-mounted stent 91*b* is unfolded via balloon 92*b*.

The difference from the device depicted in FIG. 5 is that here the catheter shell 52*b* is not embodied as a rotating drive shaft but that the OCT and the IVUS catheters with their sensors 55*b* and 54*b* rotate within the catheter shell 52*b*, as shown by the arrows in the diagram. This enables damage to the vessel wall in critical areas of the vessel to be avoided, since the rotating section of the catheter device 51*b* can no longer come into direct contact with the vessel wall.

FIG. 7 shows an inventive x-ray device 57 with a CTO catheter device, which is based on sending out high-frequency radiation. A patient not shown in this diagram is supported on a patient table 58 for treatment and radiation is emitted via a radiation source 59 in the direction of the patient table 58. The radiation is produced via a high-voltage generator 61 controlled via a system control 62. Opposite a radiation source 59 an x-ray detector 60 is arranged, which is connected in its turn with a preprocessing unit 63 for x-ray images. In addition a connection 64 is provided for physiological sensors, which is coupled to a physiological signal processing 65 in order to control ECG signals or pulse signals or the breathing and the blood pressure of a patient.

A connection 66 is made via a terminal for the CTO catheter to a signal interface 67 for the actual treatment by OCT, IVUS and the electromagnetic position sensor system. In addition there is a connection for connecting a high-frequency based CTO catheter device 68 and a data bus 69. Another version of the CTO catheter device is alternately possible. There are also preprocessing units 70 to 72 for the OCT images, the IVUS images and the electromagnetic position sensor system provided. The associated image processing units 73, 74 and 75 are also connected to the data bus 69. The power is supplied via a power supply unit 76. Furthermore an image processing unit 77 for the x-ray images is connected to the data bus 69, which features a connection to an image data store 78 for archiving and storing the recorded images. A calibration unit 79 as well as an image correction unit 80 enables interference fields or artifacts of the imaging to be taken into account. One of the elements in the image correction unit 80 is a correction processor to eliminate image artifacts caused by a stent to be introduced or a stent that has been introduced and fitted. The known structure of the stent is used for this. The images are fused and reconstructed in an image fusion and/or reconstruction unit 81. In addition there is an interface 82 to a patient data or image data system.

The image data obtained from OCT, IVUS and the position sensor system as well as the x-ray images and possible fusion images of the different imaging techniques are shown on a display unit 83 in two dimensions, three dimensions or four dimensions. The display unit 83 is connected to an input 84 for input by a user.

The subsystems and components in accordance with FIG. 7 are advantageously integrated into one device.

FIG. 8 shows a sketch for sensor readout during execution of an inventive method with the x-ray device 57 of FIG. 7. In this case the sensors of the x-ray device 57 are read out with a partial time offset and clocked. Firstly a system clock is predefined by creating individual system pulses with the pulse generation being followed by the switching of the x-ray radiation and the activation of the magnetic location. After the x-ray radiation is switched off, the x-ray detector readout occurs and at the same time the IVUS data is read out. Subsequently the OCT data is read out, with this occurring at the same time as the readout of the ECG and the data for respiration. During the readout of the IVUS data and of the x-ray detector the high-frequency energy which is being emitted to remove the vessel blockage is active. This means that the individual sensor is read out or the components of the catheter device are activated in such a way that a mutual fault can be excluded. The time-offset and clocked readout shown here is to be seen as an example for a readout avoiding interference influences.

The invention claimed is:

1. A catheter device for treating a blockage of a vessel of a patient, comprising:
    a treatment catheter;
    a stent that is mounted in a tip of the treatment catheter, wherein the tip-mounted stent and the treatment catheter are configured as an integrated unit,
    wherein the treatment catheter consists of an integrated image monitoring system,
    wherein the image monitoring system comprises an Optical Coherence Tomography (OCT) catheter and an Intravascular Ultrasound (IVUS) catheter,
    wherein an image sensor of the OCT catheter is arranged in front of or behind an image sensor of the IVUS catheter in a longitudinal direction of the catheter device,
    wherein the catheter device further comprises:
    a transparent exit area arranged on a catheter shell of the treatment catheter or a drive shaft of the OCT or IVUS catheter for passing through an ultrasound wave of the IVUS catheter or a light of the OCT catheter,
    a hollow flexible drive shaft is provided in an inner area of the catheter shell within which a signal line of the OCT or the IVUS catheter is routed, and
    wherein the stent is arranged on an expandable balloon located in the tip of the treatment catheter that unfolds the stent, or
    wherein the stent is at least partly self-unfolding.

2. The catheter device as claimed in claim 1,
    wherein a material of the stent comprises metal or bioabsorbable material,
    wherein the metal is selected from the group consisting of: a stainless steel, a nitinol, and a memory-metal alloy, and
    wherein the bioabsorbable material is selected from the group consisting of: a biological material, a magnesium material, a bio-engineering material, and a plastic.

3. The catheter device as claimed in claim 1,
    wherein the stent comprises a coating,
    wherein the coating is a nano coating or a drug agent coating, and
    wherein the drug agent coating is selected from the group consisting of: Sirolimus, Paclitaxel, Everolimus, Rapamycin, and FK 506.

4. The catheter device as claimed in claim 1,
    wherein:
        the treatment catheter is a chronic total occlusion catheter for treating a complete vessel blockage, and
        the chronic total occlusion catheter is a pincer-type catheter.

5. The catheter device as claimed in claim 1,
    wherein the Optical Coherence Tomography or the intravascular ultrasound catheter or the drive shaft is ratable.

6. The catheter device as claimed in claim 5,
    wherein an image sensor of the Optical Coherence Tomography or the Intravascular Ultrasound catheter is arranged in front of or behind a treatment unit of the treatment catheter,
    wherein the treatment unit comprises an opening for passing through the drive shaft or the signal line or the image sensor of the Optical Coherence Tomography or the Intravascular Ultrasound catheter, and
    wherein the treatment unit is selected from the group consisting of: a pincer, a coil, and a laser lens.

7. The catheter device as claimed in claim 1, wherein a three-dimensional image of the vessel is captured by rotating and simultaneously pulling or pushing the Optical Coherence Tomography or the Intravascular Ultrasound catheter.

8. The catheter device as claimed in claim 1,
    wherein the treatment catheter comprises a position sensor system,
    wherein the position sensor system is an electromagnetic system or an ultrasound-based system comprising a position sensor, and
    wherein the position sensor is arranged in an area of a tip of the catheter device.

9. The catheter device as claimed in claim 1, wherein the catheter device is:
    mechanically or magnetically automatically navigated,
    automatically introduced into the vessel or removed from the vessel, and
    coated by a coating for screening a magnetic interference or for improving a guidance of the catheter device in the vessel.

10. The catheter device as claimed in claim 1, further comprising:
    a movement sensor for detecting a movement of the patient, and
    a physiological sensor located at a tip of the catheter device for detecting a physiological status of the patient.

11. The catheter device as claimed in claim 1, further comprising a lumen for injecting a contrast medium or a flushing fluid into the vessel.

12. The catheter device as claimed in claim 1, wherein the image sensor of the Optical Coherence Tomography catheter and the image sensor of the Intravascular Ultrasound catheter rotate within a catheter shell of the treatment catheter without rotating the catheter shell of the treatment catheter.

* * * * *